(12) United States Patent
Keene et al.

(10) Patent No.: US 8,931,519 B2
(45) Date of Patent: Jan. 13, 2015

(54) PIN VALVE ASSEMBLY

(75) Inventors: Russell Keene, Sudbury, MA (US);
David R. Friswell, Upton, MA (US);
Mark Moeller, Kingston, MA (US);
Charles Murphy, Uxbridge, MA (US);
Theodore D. Ciolkosz, Milton, MA (US)

(73) Assignee: Waters Technologies Corporation, Milford, MA (US)

( * ) Notice: Subject to any disclaimer, the term of this patent is extended or adjusted under 35 U.S.C. 154(b) by 1503 days.

(21) Appl. No.: 10/597,525

(22) PCT Filed: Feb. 18, 2005

(86) PCT No.: PCT/US2005/005714
§ 371 (c)(1),
(2), (4) Date: Aug. 12, 2008

(87) PCT Pub. No.: WO2005/079543
PCT Pub. Date: Sep. 1, 2005

(65) Prior Publication Data
US 2008/0290309 A1    Nov. 27, 2008

Related U.S. Application Data

(60) Provisional application No. 60/545,829, filed on Feb. 19, 2004.

(51) Int. Cl.
*F16K 11/14* (2006.01)
*G01N 30/20* (2006.01)
*G01N 30/22* (2006.01)

(52) U.S. Cl.
CPC ............... *G01N 30/20* (2013.01); *G01N 30/22* (2013.01); *G01N 2030/201* (2013.01); *G01N 2030/202* (2013.01); *G01N 2030/204* (2013.01); *G01N 2030/207* (2013.01)
USPC ............ 137/862; 137/597; 137/872; 137/607

(58) Field of Classification Search
USPC .......... 137/597, 625.11, 625.42, 625.44, 606, 137/607, 862, 871, 872; 251/149, 149.1, 251/149.6
See application file for complete search history.

(56) References Cited

U.S. PATENT DOCUMENTS

| | | | | |
|---|---|---|---|---|
| 1,921,895 | A | * | 8/1933 | Taurisano ..................... 261/28 |
| 2,041,694 | A | | 5/1936 | Buckley |
| 2,589,373 | A | | 3/1952 | Hammock |
| 3,421,858 | A | | 1/1969 | Quinn |
| 3,480,035 | A | | 11/1969 | Szanto |
| 3,942,553 | A | | 3/1976 | Gallatin |

(Continued)

FOREIGN PATENT DOCUMENTS

| | | |
|---|---|---|
| JP | 53-116785 A | 9/1978 |
| JP | 53-142393 A | 11/1978 |
| WO | 200023734 | 4/2000 |

*Primary Examiner* — William McCalister
(74) *Attorney, Agent, or Firm* — Schmeiser, Olsen & Watts LLP (57) ABSTRACT

A pin valve assembly and a method of controlling the flow of fluids comprising a pin block housing pin valves, a fluid plate with a fluid channel for fluidically communicating with the pin valves, and a fitting block housing fittings for fluidic communication with the fluid plate and for fluidic communication with fluidic components. The fluid flow through the channels of the fluid plate are controlled by the fluidic components and the pin valves.

21 Claims, 9 Drawing Sheets

(56) References Cited

U.S. PATENT DOCUMENTS

| | | | |
|---|---|---|---|
| 3,985,019 A | 10/1976 | Boehme et al. | |
| 4,045,343 A * | 8/1977 | Achener et al. | 210/101 |
| 4,064,908 A | 12/1977 | Loe | |
| 4,224,281 A * | 9/1980 | Thieme et al. | 422/100 |
| 4,262,879 A | 4/1981 | Gonner | |
| 4,306,587 A | 12/1981 | Tchebinyayeff | |
| 4,546,794 A * | 10/1985 | Ball | 137/599.03 |
| 4,558,845 A | 12/1985 | Hunkapiller | |
| 4,655,095 A | 4/1987 | Russo et al. | |
| 4,698,998 A | 10/1987 | Varnagy | |
| 4,703,913 A | 11/1987 | Hunkapiller | |
| 4,711,268 A * | 12/1987 | Coleman | 137/597 |
| 4,723,712 A * | 2/1988 | Egli et al. | 239/307 |
| 5,085,245 A | 2/1992 | Grove | |
| 5,151,178 A | 9/1992 | Nickerson et al. | |
| 5,194,226 A | 3/1993 | Tomoff et al. | |
| 5,277,224 A * | 1/1994 | Hutton et al. | 137/597 |
| 5,320,139 A * | 6/1994 | Paul et al. | 137/565.33 |
| 5,361,802 A | 11/1994 | Kroll et al. | |
| 5,634,624 A | 6/1997 | Lacroix et al. | |
| 5,642,756 A | 7/1997 | Lawrence et al. | |
| 5,653,259 A | 8/1997 | Ramstad | |
| 5,713,333 A * | 2/1998 | Cooper et al. | 123/450 |
| 5,842,679 A | 12/1998 | Kolchinsky | |
| 5,906,223 A | 5/1999 | Pinkham | |
| 5,950,674 A * | 9/1999 | Wylie et al. | 137/597 |
| 5,954,954 A | 9/1999 | Houck | |
| 6,012,487 A * | 1/2000 | Hauck | 137/625.11 |
| 6,086,767 A | 7/2000 | Walters | |
| 6,112,767 A | 9/2000 | Pinkham | |
| 6,257,052 B1 | 7/2001 | Zelechonok | |

\* cited by examiner

PIN VALVE ASSEMBLY

CROSS REFERENCE TO RELATED APPLICATIONS

This application claims benefit of U.S. Provisional Application No. 60/545,829, filed Feb. 19, 2004, the content of which is incorporated herein by reference.

STATEMENT ON FEDERALLY SPONSORED RESEARCH

N/A

TECHNICAL FIELD

The present invention relates generally to high pressure liquid chromatography ("HPLC"), and more particularly to a valve assembly for high pressure fluids that uses pins to block flow pathways in a fluid network.

BACKGROUND OF THE INVENTION

The practice of HPLC generally requires that a molecular species to be separated or analyzed be dissolved in a liquid, the mobile phase, and conveyed by that liquid through a stationary phase. In the stationary phase, a large surface area is presented which is in intimate contact with the mobile phase. Mixtures of analyte compounds, dissolved in the mobile phase, can be separated during passage through the column by processes of adsorption or retention, which act differently on the various analyte species. The differential retention causes the analytes to elute from the column with respect to time and volume. The eluting analytes will typically transit through an in-line detector, where quantitative and/or qualitative examination of analytes will occur.

High pressure liquid chromatography solvent delivery systems are used to source either single-component liquids or mixtures of liquids at selected pressures which can range from substantially atmospheric pressure to pressures on the order of ten thousand pounds per square inch and more. The above pressures are required to force the mobile phase through the fluid passageways of a stationary phase support, where separation of dissolved analytes can occur. The stationary phase support may comprise a packed bed of particles, a membrane or collection of membranes, a microfabricated structure typically comprising an array of fluid passageways etched into a solid support, or an open column or tube.

The separation process occurring in liquid chromatography can result in the separation of an injected sample mixture into its component parts. These component parts are eluted from the column in reasonably distinct zones or bands. As these bands pass through a detector, their presence can be monitored and a detector output can be produced. This output includes a pattern of analyte concentration within the eluting bands, which can be represented by means of a time varying electric signal, and gives rise to the nomenclature of a "chromatography peak."

The utility of chromatography relies heavily on run-to-run reproducibility, such that a given analysis can be compared with an analysis of standards or calibrates with confidence in the resulting data. Known pumping systems exhibit some non-ideal characteristics which result in diminished separation performance and diminished run-to-run reproducibility.

Among the non-ideal pump characteristics exhibited in known pumping systems are, generally, fluctuations in solvent composition and/or fluctuations in volumetric flow rate. Such volumetric flow rate fluctuations in present and known HPLC pumping systems disadvantageously cause varying retention times for a given analyte. That is, the amount of time that an analyte is retained in the stationary phase fluctuates undesirably as a function of the undesirable volumetric flow rate fluctuations. This creates difficulties in inferring the identity of a sample from the retention behavior of the components. Volumetric flow rate fluctuations can result in fluctuations in solvent composition when the output of multiple pumps is summed to provide a solvent composition.

Fluctuations in solvent composition in present and known HPLC systems disadvantageously result in interactions with the systems analyte detector and produce perturbations that are detected as if they arose from the presence of a sample. In effect, an interfering signal is generated. This interfering signal is summed with the actual signal attributable to the analyte, producing errors when the quantity of an unknown sample is calculated from the area of the eluting sample peak.

The typical valve assemblies used in these high pressure fluid systems require tight tolerances and uniform performance hundreds of times under extreme working conditions. This wear results in the high wear of parts and whole assemblies leading to degradation of results.

In light of the above, the requirements imposed on HPLC solvent delivery systems are severe. New HPLC pumps and valves are typically required to deliver solvents at pressures that can range from several pounds per square inch to as much as 100,000 psig. There are problems and non-ideal effects associated with delivering liquids for chromatography against elevated pressures including seal deformation under load and absolute seal leakage. HPLC pumps are expected to output the mobile phase solvent at precisely controlled flow rates in a smooth and uniform manner. In the case of gradient chromatography, where a fixed solvent composition is blended in real time during the separation, there is the further requirement that mobile phase composition as well as flow rate be precisely and accurately controlled during delivery. However, system operating pressures may be changing very substantially during the separation and the compressibility of the constituent mobile phase solvents may be quite different. Additionally, continuous-delivery pumping systems create tremendous wear on the pumping and valve systems.

The large problems associated with the control of high pressure fluids with high precision and minimal fluid disturbance can be minimized by the use of robust, valve assemblies.

SUMMARY OF THE INVENTION

The invention involves a pin valve assembly comprising a pin block housing pin valves, a fluid plate with a fluid channel for fluidically communicating with the pin valves, and a fitting block housing fittings for fluidic communication with the fluid plate and for fluidic communication with fluidic components. The assembly has one or more fitting ports, aligned with the fittings, and one or more pin valve seats, aligned with the pin valves. The fitting ports can be integrated into the fluid channel of the fluid plate or integrated into the fittings of the fitting block. Similarly, the pin valve seats can be integrated into the fluid channel of the fluid plate or integrated into the pin valves themselves.

The pin block is preferably a substantially cylindrical stainless steel block with six bores longitudinally through. The bores may be parallel or at an angle to each other. Whatever the angle in relation to each other, the bores must place the distal pin end of a pin valve into alignment with the fluid plate thereby placing a pin valve seat in intersection with the fluid channel. If the pin valve seat is integrated into the pin valve, the placement of the pin valve must provide for the seat to intersect the channel. If the pin valve seat is integrated into the fluid channel of the fluid plate, the pin valve must sit within the pin valve seat when extended.

The six bores of the pin block provide for six pin valves to be placed in proximity to and communication with the fluid plate. The fluid plate is preferably a stainless steel, substantially cylindrical plate being much shorter than the pin block in the longitudinal or height direction. The fluid plate can be coated with a polymer. Alternatively, the fluid plate can have a substantially flat polymer shim on its proximal and/or distal surfaces. The polymer can be, but is not limited to, fluorocarbon or more preferably tetrafluoroethylene.

The plate is also preferably smaller in diameter than the pin block and formed to partially fit within a depression on the distal end of the pin block. The fluid plate can have a fluid channel that provides for a fluid sample to flow under pressure throughout its extent. Alternatively, the fluid plate can have one or more separate channels with channel ends.

In one embodiment, pin valve seats intersect the fluid channel on its proximal side such that, when a pin valve is sitting in its seat, the fluid is substantially prevented from flowing beyond that particular pin valve, hence the valve is closed. The distal side of the fluid plate is intersected with fitting ports that communicate to fluidic fittings and to the channels of the fluid plate. However, in another embodiment, the pin valve seats and fitting ports can be on the same side of the fluid plate.

The fitting block houses fluidic fittings in positions that provide fluidic communication with the fluid plate. The fittings are commonly for a sample syringe, a pump syringe, a pump, a chromatographic column and both ends of a sample loop. It is preferable that the proximal end of the fitting block be substantially cylindrical and have a depression to partially fit the fluid plate. It is also preferable that the fitting block be fitted to the pin block while holding the fluid plate in place there between. Screws, complimentary threading or other known means may hold the pin block and fitting block together.

In typical operation of the present invention, pin valves are actuated to sit on or lift from the pin valve seats blocking or allowing a fluid sample to flow through the channels of the fluid plate. Each pin valve can be housed in a standardized housing comprising a means for actuation for axially moving the pin valve to sit on the pin valve seat and substantially block fluid flow from a down stream location or remove the pin from the pin valve seat and provide for fluid flow to the down stream location. Alternatively, the pin valve seat can be integrated into the pin valve and move and perform similarly. Actuation of the pin valve places the pin valve and pin valve seat on the fluid channel of the fluid plate, to substantially block the flow of fluid through the channel.

When used as an injection valve for an HPLC system, the invention has a load position where the sample is introduced through a sample syringe in communication with a fitting port on the fluid plate. Two pin valves close the fluid channel between the pump and the column and a third closes the channel between the pump syringe and the sample syringe. Therefore, the pump syringe is able to generate negative pressure in the fluid channel across the sample loop to the sample allowing for the sample to be drawn into the sample loop. In the inject position, two pin valves are actuated to close the channels between the sample syringe and the pump syringe and a third pin valve closes the channel between the pump and column. This inject position allows the pump to inject the sample contained in the sample loop into a column in communication with fluid plate by a fitting port by pressure exerted from a pump also in communication with a fitting port.

DETAILED DESCRIPTION OF THE INVENTION

Figure 1:
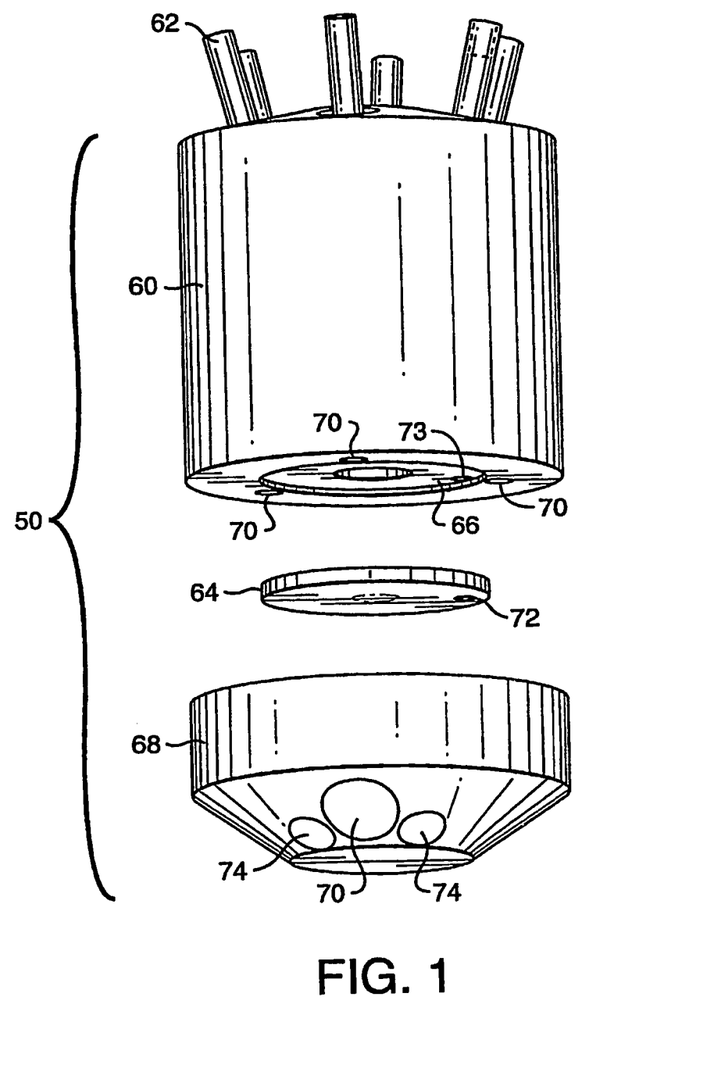
FIG. 1 is a partially exploded view of one embodiment of the present invention.
Figure 2:
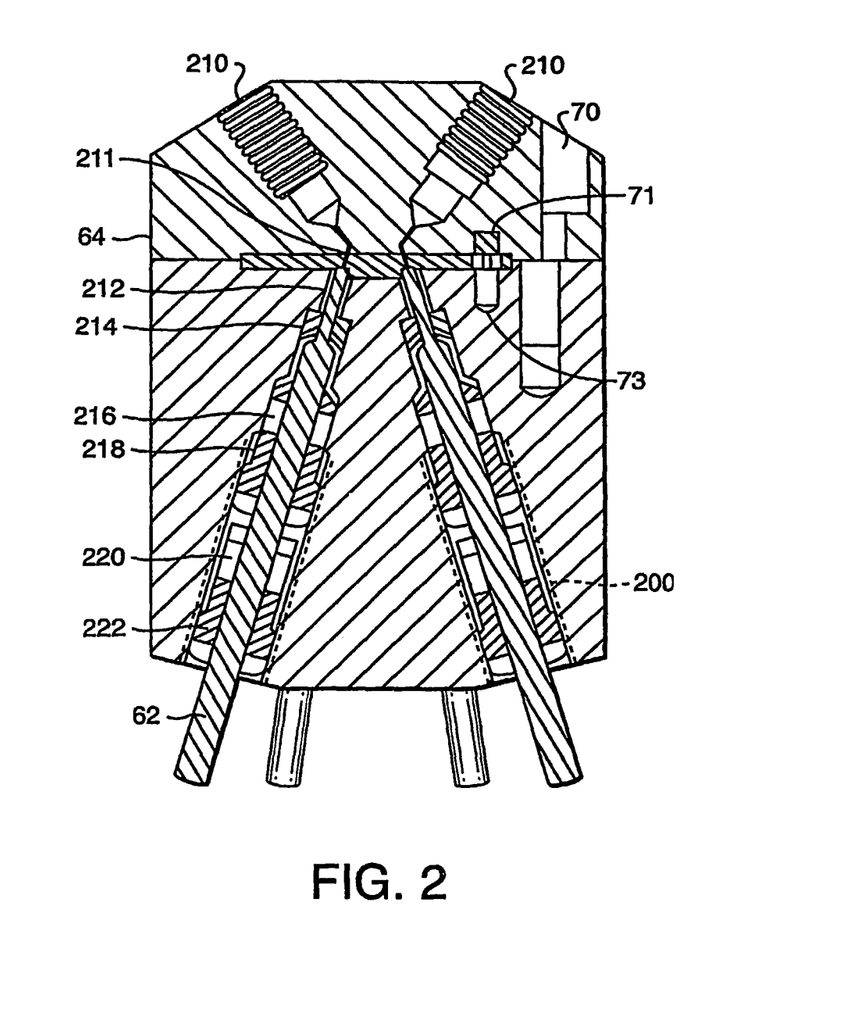
FIG. 2 is a cross sectional view of one embodiment of the present invention.
Figure 3:
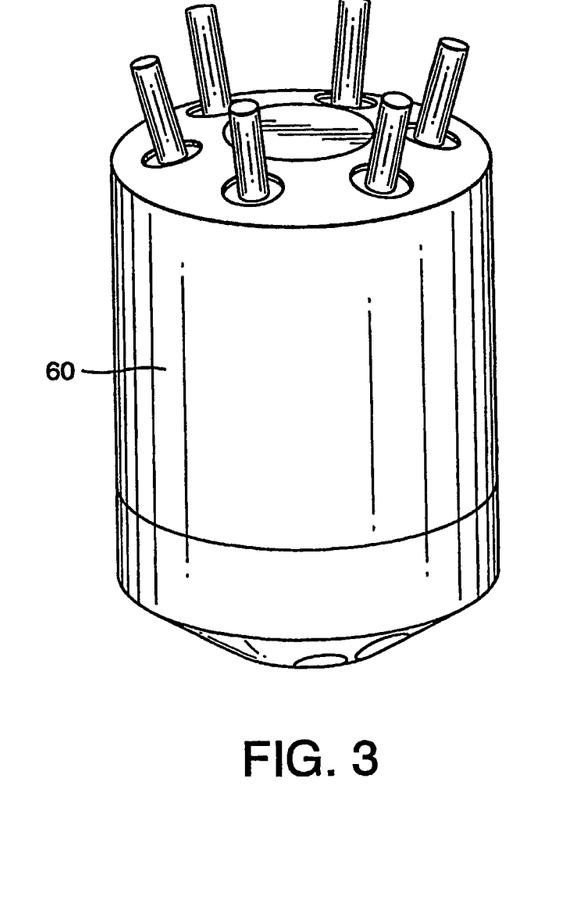
FIG. 3 is a perspective view of one embodiment of the present invention.

FIG. 1 shows an exploded view of the pin valve assembly 50 of the present invention. The pin valve assembly 50 comprises a pin block 60, which is shown with the valve pins 62 inserted into the block 60 at its proximal end. Preferably, the pin block 60 is substantially cylindrical as shown. As best seen in FIG. 2, the pin block 60 comprises one or more bores 200 or passages provided for housing the pin valves 62. FIG. 3 shows the preferred embodiment where the entrance to each bore is aligned along the circumference of the pin block 60, although this is not critical to the invention. The bores 200 extend longitudinally through the pin block 60 allowing the distal ends of the valve pins 62 to impinge on the fluid plate 64, which preferably has a smaller circumference than the pin block 60 generally. The valve pins 62 can be placed in a housing that conforms to the bores such that the fluid plate 64 is held substantially in place. In a modular embodiment, the valve pin housing and bore are releasably fitted such that a valve pin in its housing may be easily removed and replaced with another valve pin.

The pin block 60 has a recessed portion 66 at its distal end that conforms to the shape and size of the fluid plate 64. The pin block 60 also has a complimentary means for attaching to the fitting block 68. Preferably, the pin block 60 and fluid block 68 are screwed together and in the embodiment of FIG. 1, there are three screw holes one of which is partially in view 70 in FIG. 2. Additionally, an alignment pin 71 and holes 72, 73 are utilized to angularly align the fluid plate 64, pin block 60 and fitting block 68. Centering is done by the close fit of the fluid plate 64 in the recess 66 of the pin block 60.

Figure 4:
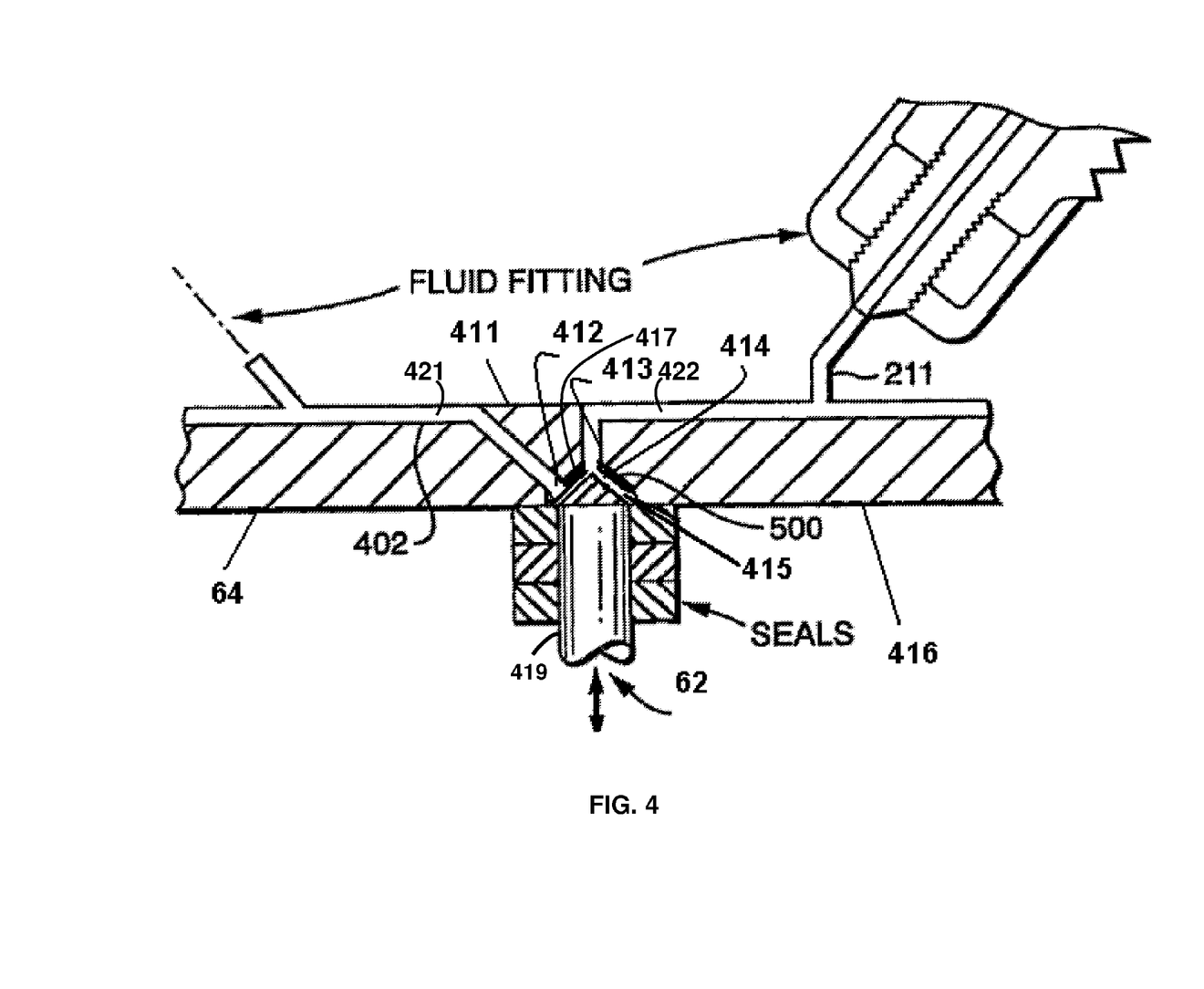
FIG. 4 is a detailed cross sectional view of a fitting port, channel and pin valve seat of one embodiment of the present invention.
Figure 5:
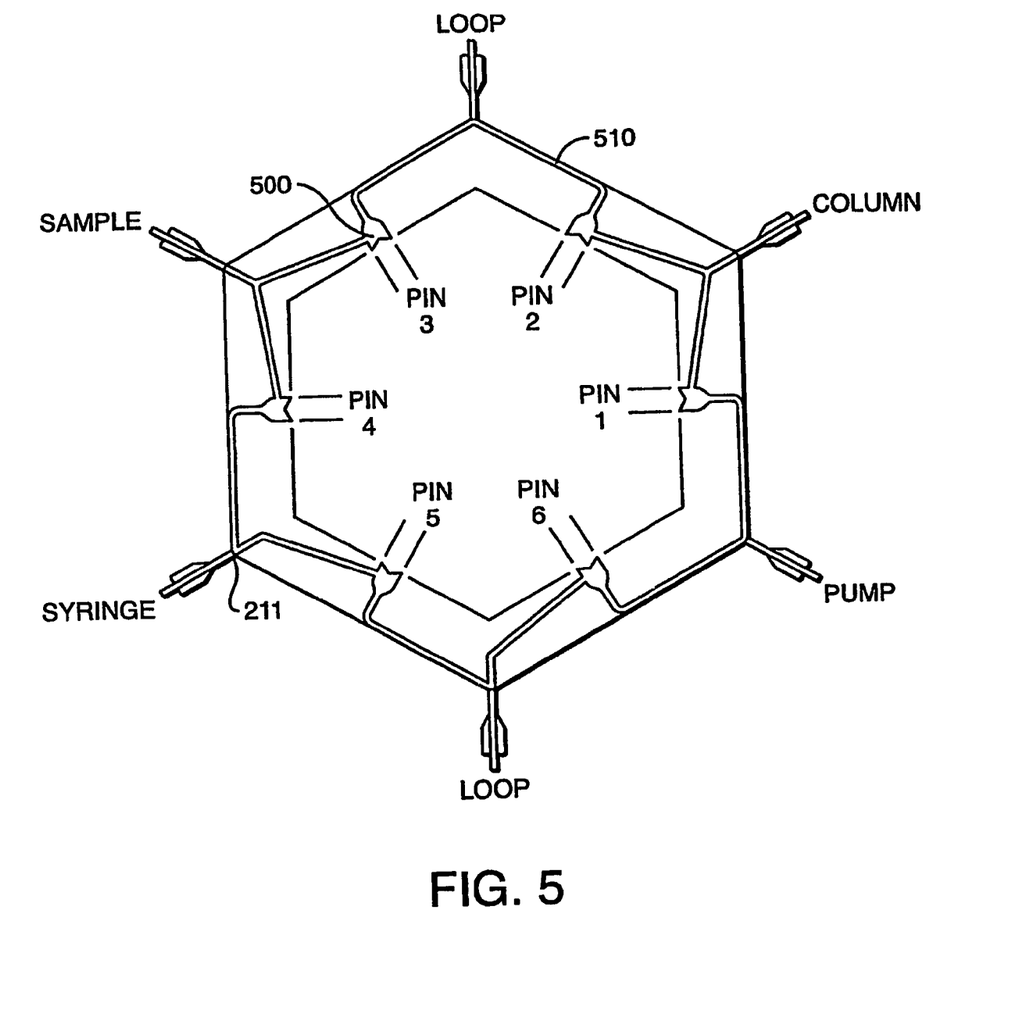
FIG. 5 is a schematic representation of one embodiment of the present invention.
Figure 9:
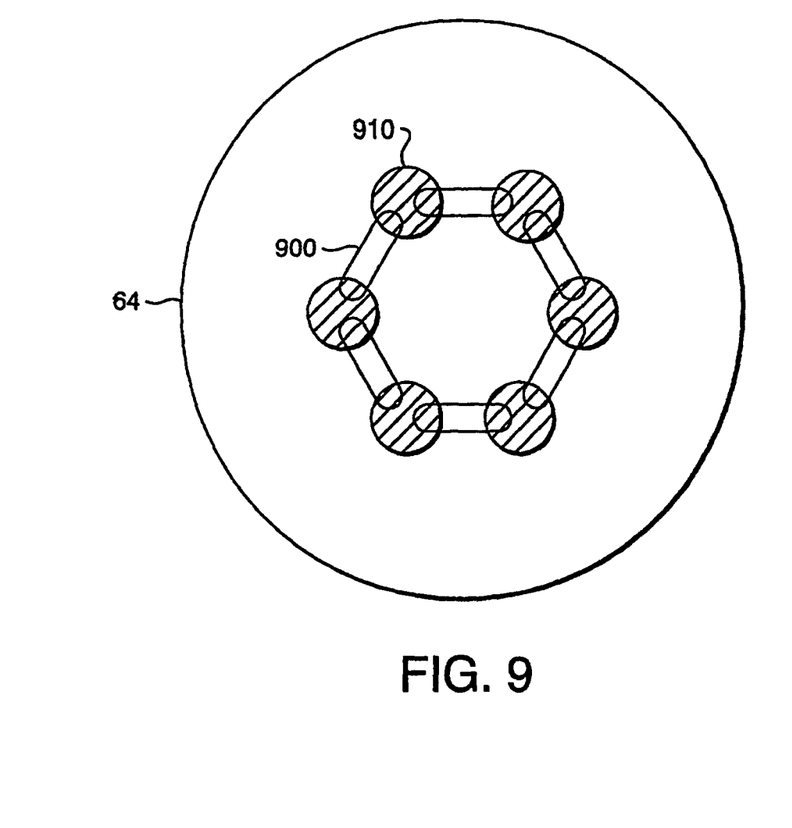
FIG. 9 is a plan view of one embodiment of a fluid plate of the present invention.

The fluid plate 64 is a substantially planar plate on which is disposed a fluid channel 510 (partially shown in FIG. 4 and shown schematically in FIGS. 5 & 9). The fluid channel can be a single circumferential channel or a plurality of channels. The channel 510 is intersected with pin valve seats 500 adapted to provide a seat for the valve pins 62 to block the fluid flowing through the channel 510. These channels 510 can be disposed to provide an interconnected track intersected by fluidic fitting ports 211 that communicate to external fluidic components such as pumps and chromatographic separation columns. Preferably, the proximal side of the fluid plate 64 has pin valve seats 500 while the distal side has the fluidic channels 510.

Figure 10:
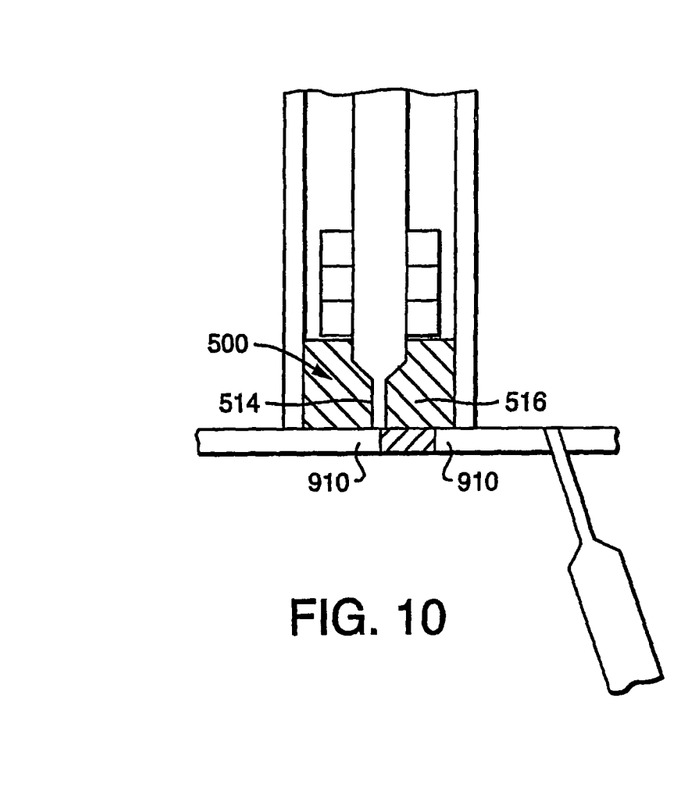
FIG. 10 is a detailed cross sectional view of a pin valve and fluid channel.

Alternatively, the fluid plate can have one or more separate channels. These channels are also intersected by fluidic fitting ports and pin valve seats. In this embodiment the structure of the pin valve seat 500 provides for fluidic communication between the separate channels. As discussed further, FIG. 10 demonstrates one embodiment of the pin valve seat having passages that communicate with separate channels.

The fitting block 68 comprises fitting bores 74 that house and align fluidic fittings 210 with the fluid plate 64. The fitting bores 74 are provided to conform to the fluidic fittings 210 and hold the fittings substantially in place such that the fittings can fluidically communicate with the fluid plate 64. The fluidic fittings 210 preferably communicate with fluidic components (not shown) such as a sample syringe, and pump syringe, both sides of a sample loop, a pump and a packed column. The sample loop can alternatively be incorporated directly into the fluid plate 64, as are the channels 510.

The pin block and fitting block are preferably stainless steel. The fluid plate is preferably stainless steel coated with a fluorocarbon polymer such as Teflon or faced with a fluorocarbon polymer shim. However, any material that can withstand the use over a reasonable period of time may be used. Other possibilities include titanium, ceramics, poly ether ether ketone (PEEK), polyphenylene sulfide (PPS), and other thermoplastics.

FIG. 2 is a cross-sectional view of the assembled pin block 60, fluid plate 64, and fitting block 68. The fluidic fittings 210 are shown in communication with the fluid plate 64 through a fluidic fitting port 211. One embodiment of this is shown in detail in FIG. 4. The pin bore 200 in cross section shows the valve pin from distal to proximal end comprising seals 212, a seal load sleeve 214, a Belleville spring 216, a nut seal 218, a second Belleville spring 220, and a nut 222.

FIG. 5 is a schematic representation of the fluid plate, fluid channel 510, fitting ports 211, fluidic components, pin valves (1-6) and pin valve seats 500 for a chromatographic application. The pin valves each sit in a pin valve seat 500 to block the flow of fluid through the channel 510 of the fluidic plate 64. When in a load stage, pin valves 3, 5, and 1 are open, while pin valves 4, 2, and 6 are closed. This allows the sample to be loaded into the sample loop and prevents the sample from entering the channels that lead to the column or pump. In an inject stage, pin valves 6, 2, and 4 are open while pin valves 1, 3, and 5 are closed. This allows the sample to be injected into the column and processed.

Referring again to FIG. 4, the fluid plate 64 has a first outer surface 411 and a second outer surface 416 opposite the first outer surface 416. The fluid plate 64 includes a hole 414 that extends through a portion of the second outer surface 416 and that intersects the fluid channel 402. The pin valve seat 500 is positioned in the hole 414 and extends from a region 415 of the hole 414 proximal the second outer surface 416 of the fluid plate 64 to intersect the fluid channel 402. In particular, the pin valve seat 500 extends to a region 417 that abuts both an opening 412 extending from the hole 414 at a first portion 421 at a left side of the fluid channel 402 at the region 415 of the hole 414 proximal the second outer surface 416 of the fluid plate 64 and an opening 413 extending from the hole 414 at a second portion 422 at a right side of the fluid channel 402 at the region 415 of the hole 414 proximal the second outer surface 416 of the fluid plate 64. When the valve pin 62 is seated in the pin valve seat 500, for example, sidewall 419 of the valve pin 62 moves linearly in and out of the fluid plate 64 as shown by arrow, both openings 412, 413 are blocked.

Figure 6:
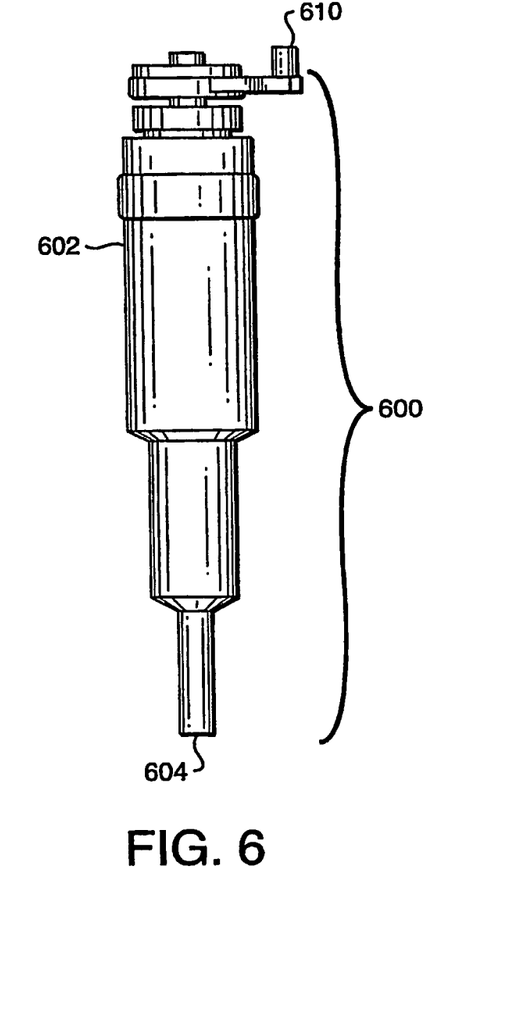
FIG. 6 is a plan view of one embodiment of the present invention.

The pin valves may be designed as a cartridge to modularize the pin valve assembly. The cartridges 600 as shown in FIG. 6 comprise a standardized housing 602 preferably of molded polyphenylene sulphide but the material may be of any known material that can properly withstand the stresses to which the invention is typically exposed. At the proximal end of the cartridge is a pin lift assembly 610 used to actuate the pin 604 to either its extended position or its unextended position. The extended position prevents fluid flow to a down stream location by extending the pin 604 from the housing 602 to sit in a pin valve seat. The unextended position has the pin 604 retracted back from the pin valve seat and preferably into the housing 602 for providing fluid flow to a down stream position. The pin pressure, seal pressure and pin lift can be controlled by a spring housed in the housing 602 or by known methods. Rotation of the lift assembly by known means provides for the spring to compress or decompress to equilibrium providing the required force to displace the pin 604 to its extended or unextended positions. Preferably, the pin 604 can be actuated, or the actuation may be assisted, pneumatically by pressurized gas using known methods.

The cartridge 600 is adapted to fit into the bores of the pin valve assembly. A key or other known means may be used to orient the cartridge 600 in the pin block. This modular design can provide for pin pressure to be adjusted by replacing a pin and housing with another pin and housing of different spring tension. Additionally, worn valves may be easily replaced using this embodiment. The modular cartridge housing 600 is complimented by the bores of the pin block 60 to be releasably fitted by known means.

Figure 7:
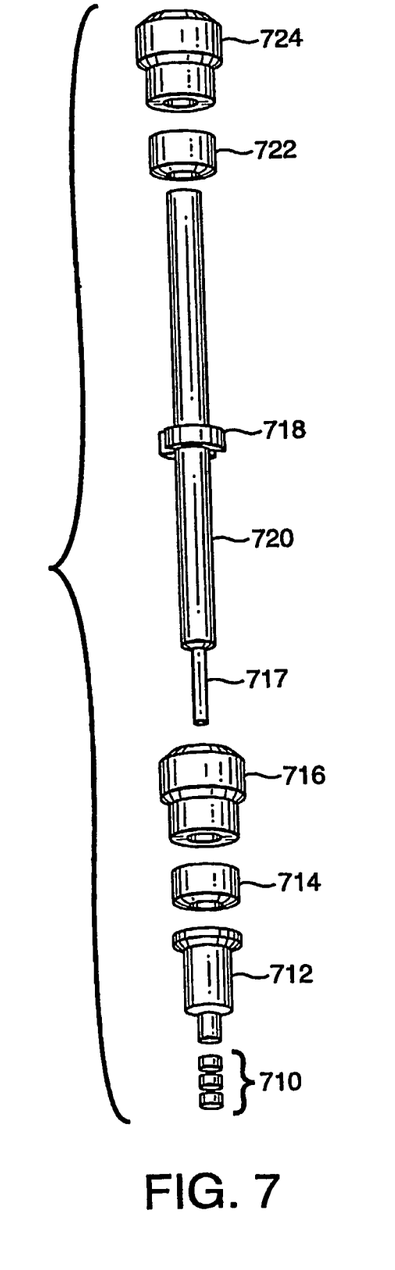
FIG. 7 is an exploded view of one embodiment of a pin valve of the present invention.

FIG. 7 provides a detailed exploded view of an embodiment of a single pin valve of the present invention. At the distal end of this embodiment is a ring seal of polytetrafluoroethylene (PTFE) surrounded by two PEEK ring seals 710. A seal load sleeve 712 houses the ring seals at its distal end and has a wider circumference at its proximal end upon which sits Belleville spring 714. A load ring 718 integral to a pin 720 holds a nut seal 716 on the Belleville spring 714. The pin has a smaller circumference portion 717 at its distal end. The pin 720, up to its load ring 718, passes through the seal nut 716, Belleville spring 714, seal load sleeve 712. The smaller circumference portion 717 of the pin 720 passes through the ring seals 710 with its most distal portion capable of impacting the fluid plate at a pin valve seat 500. On the proximal side of the load ring 718 is a second Belleville spring 722, and a nut 724 to apply axial compression force. The distal end of the pin 717 can have a diamond-like carbon coating.

Figure 8:
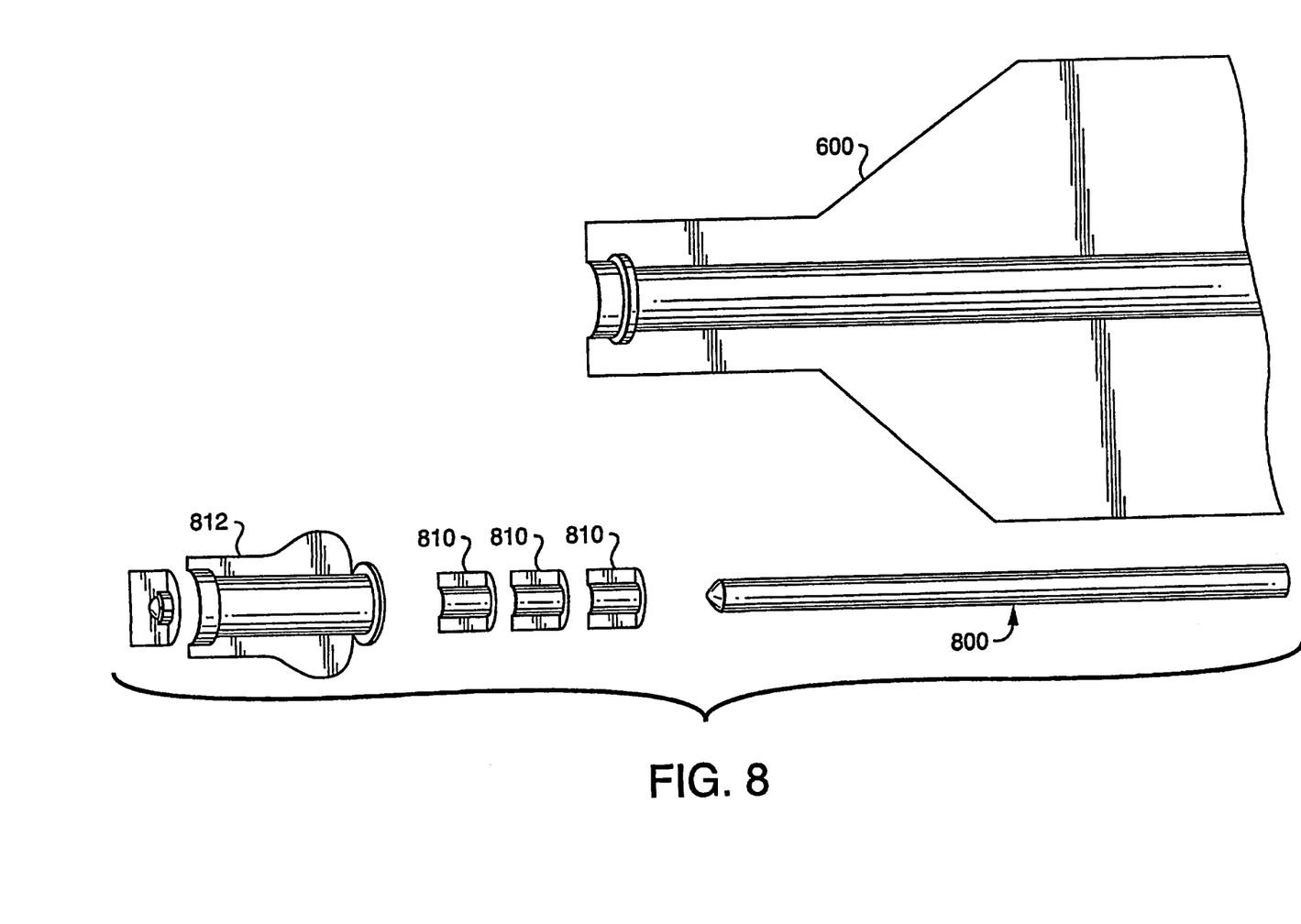
FIG. 8 is a detailed exploded view of another embodiment of a pin valve of the present invention.

FIG. 8 is a detailed exploded view of an embodiment of a pin valve in a modular, cartridge configuration. A pin 800 passes through ring seals 810 and a load sleeve 812 within the cartridge housing 602. In this embodiment, the valve seat 802 is fitted to the pin valve rather than being fitted on the fluid plate.

A further embodiment of the fluid plate is shown in FIG. 9. With the pin valve seat fitted to the pin valve the fluid plate 64 can comprise six separate channels 900. The pin valve seat can be placed in an overlapping position over two channel ends. The pin valve seat 910 as shown in detail in FIG. 10 comprises two passages 914, 916 at angles provided to reach the separate channel ends. When withdrawn, the pin allows the passages 914 and 916 to communicate. When extended, the pin substantially blocks at least one passage.

Accordingly, it should be readily appreciated that the device and method of the present invention has many practical applications. Additionally, although the preferred embodiments have been illustrated and described, it will be obvious to those skilled in the art that various modifications can be made without departing from the spirit and scope of this invention. Such modifications are to be considered as included in the following claims.

The invention claimed is:

1. A pin valve assembly comprising:
a pin block housing a valve pin configured for axial movement, the valve pin constructed and arranged for at least one of a load stage and an inject stage of a chromatography operation;
a fluid plate with a fluid channel for fluidically communicating with the valve pin, the fluid plate having a first outer surface and a second outer surface opposite the first outer surface, the fluid plate including a pin valve seat that intersects the fluid channel between a first portion of the fluid channel and a second portion of the fluid channel, wherein the fluid plate includes a smooth cylindrical surface extending from the second surface and the pin valve seat extends from the smooth cylindrical surface, the pin valve seat in alignment with the pin block housing to receive the valve pin; and
a fitting block housing a fitting for fluidic communication with the fluid plate, wherein the fitting block engages the entire first outer surface of the fluid plate and the pin block engages the entire second surface of the fluid plate,
wherein, when the valve pin is seated in the pin valve seat, the first and second portions of the fluid channel are blocked from fluidically communicating with each other.

2. A pin valve assembly as in claim 1 further comprising: a fitting port, aligned with the fitting.

3. A pin valve assembly as in claim 2 wherein: the fitting port is integrated into the fluid channel of the fluid plate.

4. A pin valve assembly as in claim 1 wherein: the pin valve seat is integrated into the fluid channel of the fluid plate.

5. A pin valve assembly as in claim 2 wherein: the fitting port is integrated into the fitting.

6. A pin valve assembly as in claim 1 wherein: the fitting block is coupled to the pin block with the fluid plate positioned between the pin block and fitting block.

7. A pin valve assembly as in claim 6 wherein: the fitting block is coupled to the pin block by a screw connection.

8. A pin valve assembly as in claim 1 further comprising a pin valve having the valve pin with distal and proximal ends substantially axially disposed in a housing.

9. A pin valve assembly as in claim 8 wherein the distal end of the pin has a diamond-like carbon coating.

10. A pin valve assembly as in claim 1 wherein: the valve pin is actuated by an actuator to provide for a distal end of the valve pin to sit in the pin valve seat substantially sealing the fluid channel and removing the distal end of the valve pin from the pin valve seat opening the fluid channel.

11. A pin valve assembly as in claim 1 wherein: the pin valve comprises a ring seal above the distal end of the valve pin and within a pin housing for providing sealing of the fluid plate.

12. A pin valve assembly as in claim 1, further comprising: fluidic components in communication with the fluid plate, the fluidic components including an HPLC system pump syringe, pump, column, sample loop and sample syringe.

13. A pin valve assembly as in claim 1 wherein: each valve pin is housed in a housing comprising an actuator for axially moving the valve pin to sit on the pin valve seat and substantially block fluid flow from a downstream location or remove the pin from the pin valve seat and provide for fluid flow to the down stream location.

14. A pin valve assembly as in claim 1 further comprising a pin valve including pin seals, a seal load sleeve, a Belleville spring, and a nut seal around a distal end of a pin below a load ring, and a second Belleville spring and a nut above the load ring.

15. A pin valve assembly as in claim 14 wherein: the pin seals are two polyetheretherketone washers surrounding a polytetrafluoroethylene washer.

16. A pin valve assembly as in claim 1 wherein: the fluid plate is stainless steel coated with a fluorocarbon polymer.

17. A pin valve assembly as in claim 16 wherein: the fluorocarbon polymer is tetrafluoroethylene.

18. A pin valve assembly as in claim 1 wherein: the fluid plate is stainless steel with a substantially flat fluorocarbon polymer shim on its surface that is sealed against pin block and fitting block.

19. A pin valve assembly as in claim 18 wherein: the fluorocarbon polymer is tetrafluoroethylene.

20. A pin valve assembly as in claim 1 wherein: the pin valve is actuated by an actuator to provide for the distal end of the valve pin to sit in the pin valve seat substantially sealing the fluid channel and removing the distal end of the valve pin from the pin valve seat opening the fluid channel.

21. A pin valve assembly as in claim 20 wherein: the actuator is pneumatically operated.

* * * * *